US009796908B2

(12) United States Patent
Hendry et al.

(10) Patent No.: US 9,796,908 B2
(45) Date of Patent: Oct. 24, 2017

(54) PROCESS FOR ENHANCING BIOGENIC METHANE PRODUCTION FROM A CARBONACEOUS MATERIAL USING A NUTRIENT COMPOSITION WITH LOW NITROGEN/HIGH PHOSPHORUS CONCENTRATIONS (71) Applicant: Commonwealth Scientific and Industrial Research Organisation, Campbell, Australian Capital Territory (AU)

(72) Inventors: Philip Hendry, Leichhardt (AU); David Midgley, Berowa (AU)

(73) Assignee: COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 0 days.

(21) Appl. No.: 14/652,945

(22) PCT Filed: Dec. 19, 2013

(86) PCT No.: PCT/AU2013/001488
§ 371 (c)(1),
(2) Date: Jun. 17, 2015

(87) PCT Pub. No.: WO2014/094055
PCT Pub. Date: Jun. 26, 2014

(65) Prior Publication Data
US 2015/0329765 A1 Nov. 19, 2015

(30) Foreign Application Priority Data

Dec. 19, 2012 (AU) ................................ 2012905562
Jul. 30, 2013 (AU) ................................ 2013902823

(51) Int. Cl.
| C09K 8/582 | (2006.01) |
| E21B 43/16 | (2006.01) |
| E21B 43/00 | (2006.01) |
| C09K 8/62 | (2006.01) |
| C09K 8/82 | (2006.01) |
| C12N 1/20 | (2006.01) |
| C12P 5/02 | (2006.01) |

(52) U.S. Cl.
CPC ............. *C09K 8/582* (2013.01); *C09K 8/62* (2013.01); *C09K 8/82* (2013.01); *C12N 1/20* (2013.01); *C12P 5/023* (2013.01); *E21B 43/006* (2013.01); *E21B 43/16* (2013.01); *Y02E 50/343* (2013.01)

(58) Field of Classification Search
None
See application file for complete search history.

(56) References Cited

U.S. PATENT DOCUMENTS

| 4,826,769 | A | * | 5/1989 | Menger | .................. | C12M 21/04 |
| | | | | | | 210/603 |
| 7,832,475 | B2 | * | 11/2010 | Jin | .......................... | B09B 3/00 |
| | | | | | | 166/246 |
| 2011/0250582 | A1 | * | 10/2011 | Gates | ..................... | C09K 8/582 |
| | | | | | | 435/3 |
| 2011/0277991 | A1 | * | 11/2011 | Toledo | .................. | C09K 8/582 |
| | | | | | | 166/246 |
| 2011/0308790 | A1 | * | 12/2011 | Strapoc | .................. | C09K 8/582 |
| | | | | | | 166/250.01 |
| 2012/0064609 | A1 | * | 3/2012 | Clement | .................. | C10G 1/00 |
| | | | | | | 435/262 |
| 2012/0115201 | A1 | | 5/2012 | Adams | | |
| 2015/0329876 | A1 | | 11/2015 | Hendry et al. | | |
| 2016/0319643 | A1 | * | 11/2016 | Lambourne | ............ | C09K 8/582 |

OTHER PUBLICATIONS

Ghasimi S. et al. The Effect of C:N:P Ratio, Volatile Fatty Acids and Na+ Levels on the Performance of an Anaerobic Treatment of Fresh Leachate from Municipal Solid Waste Transfer Station. African J of Biotechnology 8(18)4572-4581, Sep. 15, 2009.*
Wang X. et al. Effect of Nutrient Addition on an Oil Reservoir Microbial Population. Petroleum & Environmental Biotechnology 3(3)1-10, 2012.*
Davies, et al. (2000), Efficient Improvement of Silage Additives by Using Genetic Algorithms; Applied and Environmental Microbiology, 66(4), 1435-1443.
Heylen, et al. (2006), Cultivation of Denitrifying Bacteria: Optimization of Isolation Conditions and Diversity Study; Applied and Environmental Microbiology, 72(4), 2637-2643.
https://web.archive.org/web/20121030084830/http://www.dsmz.de/microorganisms/medium/pdf/DSMZ_Medium465d.pdf, published on Oct. 30, 2010 as per Wayback Engine.
https://web.archive.org/web/20121030071930/http://www.dsmz.de/microorganisms/medium/pdf/DSMZ_Medium465.pdf, published Oct. 30, 2012 as per Wayback Engine.
(Continued)

Primary Examiner — Ralph Gitomer
(74) Attorney, Agent, or Firm — Leason Ellis LLP (57) ABSTRACT A nutrient composition for enhancing biogenic methane production from a carbonaceous material is described. The nutrient composition comprises a source of phosphorus (P) and a source of nitrogen (N), wherein the molar ratio of phosphorus to nitrogen (P/N) is greater than 1.5, and the nitrogen concentration is at least 0.1 m M and less than 1.7 m M. A process for enhancing biogenic methane production from a carbonaceous material is also described. The process involves contacting the nutrient composition of the invention with the carbonaceous material for a period of time to biogenically produce methane and subsequently collecting methane from the carbonaceous material. The process may further comprise contacting the carbonaceous material with a second nutrient composition, wherein the second nutrient composition has a P/N molar ratio greater than the P/N molar ratio of the former nutrient composition.

22 Claims, 2 Drawing Sheets (56) References Cited

OTHER PUBLICATIONS

International Search Report and Written Opinion of PCT/AU13/01488 dated Jun. 23, 2015.
DSMZ GmBH, 2012—mineral culture 465d and 465 (retrieved from https://web.archive.org/web/20121030084830/http://www.dsmz.de/microorganisms/medium/pdf/DSMZ_Medium465d.pdf, and https://web.archive.org/web/20121030071930/http://www.dsmz.de/microorganisms/medium/pdf/DSMZ_Medium465.pdf).
Nazina T. et al. Regulation of Geochemical Activity of Microorganisms in a Petroleum Reservoir by Injection of Peroxide or Water-Air Mixture. Microbiology 77(3)324-333, 2008.
Shimizu S. et al. Geobiology Molecular Characterization of Microbial Communities in Deep Coal Seam Groundwater of Northern Japan. vol. 5, pp. 423-433, 2007.

\* cited by examiner

PROCESS FOR ENHANCING BIOGENIC METHANE PRODUCTION FROM A CARBONACEOUS MATERIAL USING A NUTRIENT COMPOSITION WITH LOW NITROGEN/HIGH PHOSPHORUS CONCENTRATIONS

FIELD

The present invention relates to a nutrient composition, process and system for enhancing biogenic methane production from a carbonaceous material.

BACKGROUND

Methane is associated in varying amounts with most coal deposits. It may be formed thermogenically during burial and maturation of the coal or it may be produced biogenically by the action of microbes. Bacteria are considered to be the primary degraders of coal, producing a range of intermediates which are successively degraded to methane precursors such as hydrogen gas, carbon dioxide, acetate and various others compounds (e.g. dimethyl sulfide, formate, methanol and methylamines). These precursors are then converted to methane via methanogenic archaea. This methanogenic process may occur via a number of mechanisms including $CO_2$ reduction, acetoclastic (from acetate) or methylotrophic processes.

The coal seam environment in which biogenic methane is produced is anoxic and reducing. Due to macronutrient limitation biogenic methane production is slow and occurs over long time-scales. Production from a typical coal seam methane (CSM) well may occur for 5-7 years, after which time the rate of production becomes uneconomic and the well may be abandoned.

It may be possible to prolong the production life of the well by introducing methanogenic microbial populations. US Publication No. 2004/0033557 describes introducing a consortium of selected anaerobic microorganisms into a subsurface formation for in situ conversion of organic compounds in the formation into methane and other compounds.

It may also be possible to relatively rapidly replenish the methane within a buried coal seam by stimulation of the microbes that reside in the coal and/or associated water. It is known that this can be achieved by addition of nutrients to the system. For example, U.S. Pat. No. 7,832,475 describes a method for enhancement of biogenic methane production that involves introducing an indiscriminate microbial population stimulation amendment, such as corn syrup, emulsified oil, and milk, to blanket boost microbial populations in a hydrocarbon-bearing formation. The method further involves subsequent manipulation of the microbial populations by selectively starving one or more microbial populations to selectively sustain at least one of the boosted microbial populations.

In processes designed to enhance methane production, through enhancing microbial activity through nutritional supplements, the lifecycle analysis of the whole system needs to be taken into account. For example, U.S. Pat. No. 4,826,769 discloses that microbial produced methane from coal preferably requires a ratio of C:N:P of 100:5:1. With nitrogen typically derived via energy intensive sources such as ammonia production, efficient and effective dosage regimes are needed.

Whilst significant progress has been made in increasing methane production through enhancing growth in consortia of microbes, there is still further scope for improvement.

SUMMARY

According to a first aspect, there is provided a nutrient composition for enhancing biogenic methane production from a carbonaceous material, the nutrient composition comprising a source of phosphorus (P) and a source of nitrogen (N), wherein the molar ratio of phosphorus to nitrogen (P/N) is greater than 1.5, and the nitrogen concentration is at least 0.1 mM and less than 1.7 mM.

It has been surprisingly found that the effective concentration of nitrogen required to stimulate methane production has a biomodal peak and that while increasing nitrogen concentrations generally promote greater microbial activity in regard to methane production, an enhanced methane production peak is obtainable at unexpected low nitrogen to phosphorus ratios as taught in the present invention.

Preferably, the nutrient composition further comprises one or more methanogenic microbial populations. More preferably the one or more methanogenic microbial populations comprises microbes selected from the group consisting of Methanobacteria, Methanococci, Methanomicrobia, Methanopyri.

The term 'carbonaceous material' is broadly used to refer to any carbon-containing substance capable of supporting, and are preferably present or provided with, one or more methanogenic microbial populations. The carbonaceous material may be subject to degradation by said one or more methanogenic microbial populations to produce methane or methane precursors. Suitable examples of carbonaceous material include, but are not limited to, coal, lignite, peat, drill cuttings, waste coal, coal derivatives, oil shale, oil formations, tar sands, hydrocarbon-contaminated soil and petroleum sludges. The carbonaceous material preferably comprises at least 0.5 wt % N and more preferably at least 1.0 wt % N on a dry ash-free basis.

The carbonaceous material may be in-situ carbonaceous material or ex-situ carbonaceous material. In-situ carbonaceous material may refer to carbonaceous material residing in an original source location such as a subterranean formation, or goaf bearing carbonaceous material. Ex-situ may refer to a carbonaceous material that has been removed from its original source location. Ex-situ carbonaceous material may exist in a reactor, a bioreactor, a heaped pile or alternative above ground structures, a pit, and so forth.

The relatively high ratio of phosphorus to nitrogen (P/N) in the nutrient composition is unexpected, particularly given that microbes are typically composed of more than about 10 fold more N relative to P. In some embodiments, the ratio of phosphorus to nitrogen (P/N) may be greater than 2. The ratio of phosphorus to nitrogen (P/N) may be less than 8.

The nutrient composition may comprise a nitrogen concentration of at least 0.2 mM. In one embodiment the nitrogen concentration may be less than 1.6 mM. In another embodiment the nitrogen concentration may be less than 1.5 mM. In another embodiment the nitrogen concentration may be less than 1.0 mM. In a further embodiment the nitrogen concentration may be less than 0.5 mM.

The nutrient composition may comprise a phosphorus concentration of at least 1.5 mM, preferably at least 1.7 mM and more preferably at least 2 mM.

In situ carbonaceous material may co-exist with associated water or formation water. Accordingly, it will be appreciated that in some embodiments the nutrient composition may undergo dilution with said associated water.

Accordingly, in a second aspect there is provided a concentrate for producing a nutrient composition, the concentrate being formulated to provide upon dilution with liquids associated with the carbonaceous material, a nutrient composition having an effective P/N molar ratio greater than 1.5, and an effective nitrogen concentration is at least 0.1 mM and less than 1.7 mM.

An effective P/N molar ratio is determined by the respective molar concentrations of phosphorus and nitrogen in any solution, emulsion, colloidal suspension, or gel that it is in contact with or proximal to the carbonaceous material. Similarly, an effective nitrogen concentration refers to the nitrogen concentration of any solution, emulsion colloidal suspension, or gel that is in contact with or proximal to the carbonaceous material. It will be understood that prior to coming into contact with or being disposed proximal to the carbonaceous material, such solutions, emulsions, colloidal suspensions, or gels may undergo dilution with fluids associated with said carbonaceous material in the course of being brought into contact therewith.

It will be understood that the ratios and concentrations of phosphorus and nitrogen defined above are based on injecting the concentrate into an in situ carbonaceous material according to a plug flow model. It will be appreciated that other delivery models may be employed and consequently, the molar ratios and concentrations of phosphorus and nitrogen in the concentrate (and the nutrient composition) may vary depending on the various parameters and conditions of the delivery model.

According to a third aspect, there is provided a process for enhancing biogenic methane production from a carbonaceous material comprising the steps of:

contacting a nutrient composition, comprising a source of phosphorus (P) and a source of nitrogen (N), wherein the molar ratio of phosphorus to nitrogen P/N is greater than 1.5, and an effective nitrogen concentration is at least 0.1 mM and less than 1.7 mM, or as otherwise defined above, with the carbonaceous material for a period of time to biogenically produce methane; and, collecting methane from the carbonaceous material.

Preferably, the nutrient composition is in intimate contact with the carbonaceous material to enable the nutrient composition to be readily available to the methanogenic microbial populations inhabited therein.

Preferably, contacting said nutrient composition with the carbonaceous material is achieved through mixing or agitating of the nutrient composition through existing environment proximate to the carbonaceous material (e.g. formation water).

Contacting the nutrient composition with the carbonaceous material may be achieved through adjusting the injection pressure of the nutrient composition into the carbonaceous material through know techniques available to those skilled in the relevant art.

In a preferred embodiment, contacting the nutrient composition with the carbonaceous material is achieved through sub-surface flow manipulation techniques, such as those disclosed in WO2011/017771, which is incorporated herein by reference.

Preferably, the period of time in which the nutrient composition is in intimate contact with the carbonaceous material is at least one week, more preferably at least 2 weeks, even more preferably at least 3 months, yet even more preferably at least 6 months, and most preferably at least one year. In general, the longer the time the nutrient combination is in contact with the carbonaceous material, the greater the amount of methane will be produced for collection. Commercial consideration may at least partially drive the period of time at which the nutrient composition is contacted with the carbonaceous material prior to the collection of methane from the carbonaceous material.

Within a preferred embodiment of the third aspect, the process further comprises the step of contacting a second nutrient composition with the carbonaceous material for a period of time to biogenically produce methane, said second nutrient composition contacting the carbonaceous material after said first nutrient composition contacts carbonaceous material.

Within this preferred embodiment, the first nutrient composition is thought to increase activity the microbial populations to an extent that the microbial population releases sufficient nitrogen within the carbonaceous material, such that additional nutritional supplements are effective in enhancing methane production with lower nitrogen concentrations or no nitrogen at all. The first nutrient composition may function to re-activate a relatively dormant microbial population, with the second nutrient composition supplementing the nutritional needs of a re-invigorated microbial population.

The second nutrient composition preferably comprises an effective P/N ratio greater than the P/N ratio of the first nutrient composition.

The nitrogen concentration in the second nutrient composition is preferably lower than the nitrogen concentration in the first nutrient composition.

The second nutrient composition preferably comprises substantially no nitrogen. For the purposes of the present invention, substantially no nitrogen in the nutrient compositions means nitrogen levels which are no more than trace amounts, corresponding to impurities levels of other constituents making up the nutrient composition.

The time delay between the contacting of the first and second nutrient compositions with the carbonaceous material is preferably at least 1 week, more preferably at least one month and even more preferably at least two months. The maximum time delay between the contacting the first and second nutrient composition with the carbonaceous material is preferably less than one year and more preferably less than 6 months.

'Enhancing biogenic production of methane' may refer to increasing the volume of biogenic methane produced from the carbonaceous material in a given period relative to the volume of biogenic methane produced from the carbonaceous material in the absence of the nutrient composition in the same period. Alternatively, 'enhancing biogenic production of methane' may refer to accelerating the rate of production of biogenic methane from the carbonaceous material relative to the rate of production of biogenic methane produced from the carbonaceous material in the absence of the nutrient composition.

Enhancing biogenic production of methane may be achieved by increasing the size of the one or more methanogenic microbial populations or by increasing the rate of methanogenesis in said microbial populations.

The one or more methanogenic microbial populations may be any microbial population capable of methanogenesis, in other words which is capable of degrading the carbonaceous material to produce methane or methane precursors such as hydrogen gas, carbon dioxide, acetates and other organic compounds such as formates, methanol and methylamines.

Said microbial populations may be indigenous microbial populations which naturally occur or co-exist with the carbonaceous material.

Alternatively, or additionally, the methanogenic microbial populations may be introduced to the carbonaceous material. The introduced methanogenic microbial populations may be indigenous with respect to a separate or alternative carbonaceous material. Alternatively, the introduced methanogenic microbial populations may be from a bioreactor or engineered microbial cultures. Engineered microbial cultures include those produced through classical selection methods or other genetic modification methods.

According to a fourth aspect, there is provided a biogenic methane production system comprising:
- a nutrient composition for enhancing biogenic methane from a carbonaceous material comprising a source of phosphorus (P) and a source of nitrogen (N), wherein the molar ratio of phosphorus to nitrogen P/N is greater than 1.5, and an effective nitrogen concentration is at least 0.1 mM and less than 1.7 mM;
- a delivery system for delivering said nutrient composition to the carbonaceous material; and,
- a collector for collecting methane from the carbonaceous material.

BRIEF DESCRIPTION OF THE FIGURES

Notwithstanding any other forms which may fall within the scope of the nutrient composition, process and system as set forth in the Summary, specific embodiments will now be described, by way of example only, with reference to the accompanying figures in which.

DETAILED DESCRIPTION

In one aspect, the present application relates to a nutrient composition for enhancing biogenic production of methane from a carbonaceous material.

Nutrient Composition

The nutrient composition for enhancing biogenic methane production from a carbonaceous material comprises a source of phosphorus (P) and a source of nitrogen (N), wherein the molar ratio of phosphorus to nitrogen P/N is greater than 1.5, and an effective nitrogen concentration is at least 0.1 mM and less than 1.7 mM.

In some embodiments, the molar ratio of phosphorus to nitrogen (P/N) is greater than 2. The molar ratio of phosphorus to nitrogen (P/N) may be less than 8.

Interestingly, the inventors have found that the yield of methane declines at high nitrogen concentrations. They speculate that this may be possibly due to increased growth of the one or more microbial populations which diverts energy and/or carbon flux away from the production of methane. In this respect, the total combined concentration of phosphorus and nitrogen in the nutrient composition may not exceed 10 mM.

The nutrient composition may comprise a phosphorus concentration of at least 1 mM, preferably at least 1.5 mM and more preferably at least 2 mM.

The nutrient composition may comprise a nitrogen concentration of at least 0.2 mM.

In one embodiment the nitrogen concentration may be less than 2.0 mM. In one embodiment the nitrogen concentration may be less than 1.5 mM. In another embodiment the nitrogen concentration may be less than 1.0 mM. In a further embodiment the nitrogen concentration may be less than 0.5 mM.

The nutrient composition may be a liquid in the form of a solution, in particular an aqueous solution. The solvent (source of watr) in the aqueous solution may be water, deionised water, ultrapure water, distilled water, municipal water, groundwater, produced water, formation water, recycled water, process water, wastewater, brackish water or brine.

Preferably, the aqueous solution comprises formation water or of a composition similar thereto. Through using an aqueous solution the same or similar to the formation water around the carbonaceous deposit, the amended (i.e. nutrient rich) aqueous solution is better able to deliver enhanced nutrients to the microbial population without a significant lag time to adapt to the new aqueous environment.

Preferably, the temperature, pH and/or ionic strength of the source of water is substantially the same as the temperature, pH and/or ionic strength of the resultant nutrient composition.

For the purposes of the present invention, substantially the same temperature is preferably a temperature difference of no more than 20° C., and more preferably 10° C.

For the purposes of the present invention, substantially the same pH is preferably a pH difference of no more than 2, more preferably no more than 1 and even more preferably no more than 0.5.

Preferably, the pH of the nutrient composition is in the pH range of 5.0 to 10.0, more preferably 6.0 to 9.0 and even more preferably 7.0 to 8.0.

For the purposes of the present invention, substantially the same ionic strength is preferably an ionic strength difference of no more than 100%, more preferably no more than 50% and even more preferably no more than 10%.

Preferably, the nutrient composition is substantially free of oxygen (i.e. anoxic).

In some embodiments, prior to formulation of the nutrient composition, the formation water (or other solvents) may be stored in a storage reservoir such as a storage tank or a dam. Accordingly, it will be appreciated that in these particular embodiments the formation water may need to first undergo treatment to remove oxygen therefrom. Such treatments may include, but is not limited to, purging the formation water (or other solvents) with a gas such as nitrogen or a similar inert gas to displace oxygen therein.

It will be appreciated that the source of phosphorus and the source of nitrogen may be selected to be soluble in the aqueous solution. It will also be appreciated that the solubility of the source of phosphorus and/or the source of nitrogen may be enhanced in the aqueous solution with an emulsifying agent. Accordingly, the nutrient composition may further comprise an emulsifying agent.

In an alternative embodiment, the nutrient composition may be an emulsion such as an oil-in-water emulsion, or a colloid, or a suspension, or a gel.

In various embodiments the nutrient composition may further comprise at least one trace element selected from the group comprising iron, manganese, cobalt, zinc, molybdenum, nickel, aluminium, boron, copper, tungsten and selenium. The trace element may be present in the nutrient composition as an aqueous soluble salt thereof. The concentration of each trace element in the nutrient composition may be less than 200 ppm.

In other embodiments the nutrient composition may further comprise at least one vitamin selected from the group comprising pyridoxine, aminobenzoic acid, pantothenate, nicotinic acid, riboflavin, thiamine, thioctic acid, biotin, folic acid, pyruvate, and B12. The concentration of each vitamin in the nutrient composition may be less than 100 ppm.

In further embodiments the nutrient composition may further comprise at least one stimulant. Stimulants may be any factors that can be used to increase or stimulate the biogenic production of methane in the carbonaceous material. Examples of stimulants include, but are not limited to, yeast extract, Coenzyme M, lactic acid, mineral amendments (such as chloride, sodium, potassium, magnesium and calcium), alkyl alcohols, methanol, ethanol, 2-propanol, 2,3 butanediol, vanillate, glycine, cysteine, 3,4,5-trimethoxybezoate, cellulose, cinnamic acid, benzoic acid, chitin, chitosan, chlorate, perchlorate, and any combinations thereof.

Other additives may also be comprised in the nutrient composition for various purposes, for example to stabilise the nutrient composition against deterioration over time and prolong shelf life, maintain constant pH, and so forth. Such additives may include, but are not limited to, acids, bases, buffering agents, oxidants, anti-oxidants, surfactants, emulsifying agents, gelling agents, any combination thereof and the like.

Source of Phosphorus

The source of phosphorus in the nutrient composition may be any substance containing phosphorus in a form that is bioavailable to the one or more methanogenic microbial populations and has the effect of stimulating the biogenic production of methane. The method of determining whether a particular source of phosphorus has a stimulatory effect is well known to those skilled in the art.

In various embodiments, the source of phosphorus may be phosphorus containing compounds such as salts of phosphorus oxoacids, phospholipids or derivatives thereof, organophosphate esters, and any combination thereof and the like.

Examples of suitable salts of phosphorus oxoacids including, but not limited to, salts of hypophosphorus acid ($H_3PO_2$), phosphorus acid ($H_3PO_3$), metaphosphorus acid ($HPO_2$), orthophosphorus acid ($H_3PO_3$), metaphosphoric acids ($(HPO_3)_n$), polyphosphoric acids ($(HPO_3)_{n+2}$), tripolyphosphoric acid ($H_5P_3O_{10}$), pyrophosphoric acid ($H_4P_2O_7$), orthophosphoric acid ($H_3PO_4$), and the like.

Examples of suitable phospholipids include, but are not limited to, lecithin wet gum, lecithin, cephalin, phosphatidate, phosphatidylserine, phosphatidylinositol, phosphatidylinositol phosphate, phosphatidylinositol bisphosphate, phosphatidylinositol triphosphate, ceramide phosphorylcholine, ceramide phosphorylethanolamine, ceramide phosphorylglycerol, and the like.

Examples of suitable phospholipid derivatives include, but are not limited to, natural phospholipid derivatives found in eggs, soy, hydrogenated soy, or synthetic phospholipid derivatives of phosphatidic acid, phosphatidylcholine, phosphatidylglycerol, phosphatidylethanolamine, phosphatidylserine, PEG phospholipids, and the like.

Examples of suitable organophosphate esters include, but are not limited to, trixylenyl phosphate ester, butylated phenol phosphate ester, isopropyl phenol phosphate ester, and the like.

Source of Nitrogen

The source of nitrogen in the nutrient composition may be any substance containing nitrogen in a form that is bioavailable to the one or more methanogenic microbial populations.

In various embodiments, the source of nitrogen may be an inorganic nitrogen compound such as nitrogen hydrides and salts thereof, nitrogen oxoacids and salts thereof, urea, carbamide, hydroxylamine, sulfamide, thiocyanate salts, any combination thereof and the like.

Examples of suitable nitrogen hydrides include, but are not limited to, ammonia, azanes such as hydrazine, triazane and so forth, diazene, trizene, and the like.

Examples of suitable salts of nitrogen oxoacids include, but are not limited to, salts of hyponitrous acid ($H_2N_2O_2$), nitrous acid ($HNO_2$), nitroxyl (HNO), nitric acid ($HNO_3$), peroxynitrous acid ($HONO_2$), any combination thereof and the like.

In other embodiments, the source of nitrogen may be an organic nitrogen compound such as amines and ammonium salts thereof, amides, amino acids, peptides, oligopeptides, proteins, any combination thereof and the like.

In alternative embodiments, the source of nitrogen may be a nitrogen compound which is a gas phase at ambient temperature and pressure. Said gaseous nitrogen compounds may also be soluble in aqueous solutions at ambient temperature and pressure. Illustrative examples of such gaseous nitrogen compounds include ammonia, nitrogen, and nitrogen oxides. In particular when the nutrient composition may be employed to enhance methanogenic production of methane in subterranean formations bearing carbonaceous material, it is anticipated that the solubility of said gaseous nitrogen compounds in the nutrient composition is likely to increase in response to increased temperature and pressure in said subterranean formation.

It will be understood by the person skilled in the art that suitable sources of phosphorus or nitrogen may vary dependent upon the methanogenic microbial population and the carbonaceous material. The selection of suitable sources of phosphorous and nitrogen may be readily performed through a screening process in which the effectiveness of various nutrient compositions is tested upon specific carbonaceous material and methanogenic microbial populations.

Process for Enhancing Biogenic Methane Production

The nutrient composition described in the application may be employed in a process for enhancing biogenic methane production from a carbonaceous material.

The process comprises contacting said nutrient composition with the carbonaceous material for a period of time to biogenically produce methane, and collecting methane from the carbonaceous material.

Contacting the Nutrient Composition with the Carbonaceous Material

It will be appreciated by persons skilled in the art that the manner for contacting the nutrient composition with the carbonaceous material will depend on whether the carbonaceous material may be an in situ carbonaceous material or an ex situ carbonaceous material.

For example, contacting the nutrient composition with an in situ carbonaceous material in the form of a subterranean formation bearing carbonaceous material (e.g. coal seam) may comprise injecting the nutrient composition into or proximal to naturally occurring or artificially induced fractures or cleat systems in the in situ carbonaceous material by injection techniques well understood by those skilled in the art of recovering CSM including, but not limited to, injection under pressure, by gravity forces, other water injection methods and the like.

Similarly, where the in situ carbonaceous material comprises an oil shale formation, contacting the nutrient composition may comprise injecting the nutrient composition through the fractures of the oil shale formation. In another embodiment, contacting the nutrient composition may comprise injecting the nutrient composition together with a hydraulic fracturing fluid, sand propant and various chemicals. In this way, the nutrient composition may be delivered to fractures in the carbonaceous material at the same time as the fractures are caused to form under high pressure from the hydraulic fracturing fluid and/or sand propant. In the latter embodiment, the use of hydraulic fracturing fluids under anoxic or suboxic conditions is preferred so that anoxic conditions in the fractures are maintained, or can be readily attained soon afterwards.

An alternative embodiment for contacting the nutrient composition with the in situ carbonaceous material comprises providing one or more laterals to access the in situ carbonaceous material and injecting the nutrient composition (or concentrate) into the laterals. Laterals may be provided roughly parallel (horizontal) to the tops and bottoms of in situ carbonaceous material. These laterals may be either drilled outwardly from a main well bore or may be generated through high-pressure water technology. High-pressure water jet technology may be suitably used to drill laterals through friable or more porous subsurface formations. Horizontally-drilled and/or water-jet laterals may extend hundreds or thousands of meters from the main well bore, and therefore, provide much better access to the carbonaceous material. Furthermore, particularly in porous subsurface formations, injected nutrient composition (or concentrate) will tend to move through a permeable or porous subsurface formation under capillary action, thereby migrating into smaller fractures and microfractures in the carbonaceous material.

It will be appreciated that injecting the nutrient composition (or concentrate) may be continuous or intermittent. Further, injecting the nutrient composition (or concentrate) may cease entirely after an initial period, said period being sufficient to bring a sufficient volume of nutrient composition (or concentrate) into contact with the carbonaceous material.

In situ carbonaceous material may co-exist with associated water or formation water. In the case of fractured oil shale formations there may also be some hydraulic fracturing fluid associated with the carbonaceous material. The presence of these fluids in or proximal to the carbonaceous material may serve to dilute the nutrient composition. Accordingly, it will be appreciated that in some embodiments contacting a nutrient composition may comprise delivering a concentrate to the carbonaceous material, whereby the delivered concentrate undergoes dilution with fluids associated with the carbonaceous material to provide a nutrient composition wherein the molar ratio of phosphorus to nitrogen (P/N) is greater than 1.5, and the effective nitrogen concentration is at least 0.1 mM and less than 1.7 mM. The concentrations of the source of phosphorus and the source of nitrogen in the concentrate may be calculated according to the known or estimated degree of dilution.

With respect to ex situ carbonaceous material, the manner for contacting the nutrient composition with the carbonaceous material may vary.

For example, in embodiments where the ex situ carbonaceous material may be arranged in a heaped pile, contacting the nutrient composition with the heaped pile of carbonaceous material may comprise applying the nutrient composition to an outer surface of the heaped pile in an amount sufficient to cause the nutrient composition to flow or trickle under gravity from the outer surface through underlying carbonaceous material in the heaped pile.

The amount of nutrient composition that may be applied to the heaped pile may be calculated by considering the height and volume of the heaped pile, particle size of the carbonaceous material, and like factors.

Preferably, the nutrient composition is applied to the heaped pile of carbonaceous material under an anoxic atmosphere. In one embodiment, the anoxic atmosphere comprises inert gases or spent combustion gases (i.e. flue gases). Within this latter embodiment, the combustion gases, which predominantly comprise nitrogen gas and carbon dioxide may be further treated to remove minor and trace components which may have a detrimental effect on the methanogenic microbial population.

In other embodiments, where the ex situ carbonaceous material may be in a reactor (or bioreactor), contacting the nutrient composition to the carbonaceous material may comprise mixing the nutrient composition with the carbonaceous material in the reactor (or bioreactor). It will be appreciated that mixing may be continuous or intermittent. Further, mixing may cease entirely after an initial mixing period, said period being sufficient to bring the nutrient composition into contact with the carbonaceous material.

Preferably, the nutrient composition is mixed with the carbonaceous material in the reactor (or bioreactor) under an anoxic atmosphere as described above.

Period of Time to Biogenically Produce Methane

The period of time to biogenically produce methane will vary according to several factors including, but not limited to, environmental conditions, the nature and size of the carbonaceous material, and the nature and size of the one or more microbial populations.

It will generally be understood that an incubation period may be required. The incubation period may extend from the time of delivering the nutrient composition to the carbonaceous material to the time at which biogenic methane production is increased relative to biogenic methane production in the absence of the nutrient composition. The one or more microbial populations may grow to a sufficient size to enhance biogenic methane production during the incubation period. The incubation period may extend around weeks to years, although this may vary according to the aforementioned factors.

Collecting Methane

It will be appreciated by persons skilled in the art that the manner for collecting the methane will depend on whether the carbonaceous material may be an in situ carbonaceous material or an ex situ carbonaceous material.

In respect of in situ carbonaceous material, the techniques for collecting methane are well understood by those skilled in the art of recovering CSM and associated gas from various recovery wells of oil and gas bearing subterranean formations. For example, to extract the gas, a steel-encased hole may be drilled into the coal seam (100-1500 meters below ground). As the pressure within the coal seam declines due to natural production or the pumping of water from the coalbed, both gas and 'produced water' come to the surface through tubing. Then the gas is sent to a compressor station and into natural gas pipelines. Similarly, in respect of ex situ carbonaceous material, the techniques for collecting methane are well understood by those skilled in the art of recovering biogas from reactors, bioreactors, heaped piles, and so forth. For example, the ex situ carbonaceous material may be confined in a closed space to retain the biogenic methane in a headspace thereof. The closed space may be defined by a shell disposed over the ex situ carbonaceous material, or any suitable covering such as a tarpaulin. The methane may be withdrawn from the headspace under positive or negative pressure.

System for Enhancing Biogenic Methane Production

The biogenic methane production system comprises:
the nutrient composition as described in the application;
a delivery system for contacting said nutrient composition with the carbonaceous material; and,
a collector for collecting methane from the carbonaceous material.

Delivery System for Contacting Said Nutrient Composition with the Carbonaceous Material It will be appreciated by persons skilled in the art that the delivery system for contacting the nutrient composition with the carbonaceous material will depend on whether the carbonaceous material may be an in situ carbonaceous material or an ex situ carbonaceous material.

Preferably the delivery system is an anoxic delivery system.

The delivery system for contacting the nutrient composition with an in situ carbonaceous material may comprise an injection system for injecting the nutrient composition into or proximal to the in situ carbonaceous material. Such systems are well understood by those skilled in the art of recovering CSM and may include, but are not limited to, injection under pressure, by gravity forces, other water injection methods and the like. In some embodiments, such systems may be adapted to co-inject the nutrient composition with a further injection fluid, such as a hydraulic fracturing fluid.

With respect to ex situ carbonaceous material, the delivery system for contacting the nutrient composition with the carbonaceous material may vary.

In some embodiments the delivery system for contacting the nutrient composition to a heaped pile of carbonaceous material (or an above ground structure of carbonaceous material) may comprise an applicator for applying the nutrient composition to the outer surface of the heaped pile (or the above ground structure). Suitable applicators include, but are not limited to, a drip system disposed above the heaped pile or said structure.

The drip system may be operatively associated with a liquid volume controller, a plurality of sensors and so forth to control the amount of nutrient composition applied to the heaped pile or said structure. The liquid volume controller, sensors and so forth may be programmed to ensure that the nutrient composition is applied in a sufficient amount to cause it to flow or trickle under gravity from the outer surface of the heaped pile or said structure through the underlying carbonaceous material.

The heaped pile may also be confined in a closed space to maintain the heaped pile in an anoxic atmosphere. The anoxic atmosphere may comprise a gas (such as an inert gas) or a gas mixture (such as flue gas), which substantially excludes oxygen ($O_2$). The closed space may be defined by a shell disposed over the heaped pile, or any suitable covering such as a tarpaulin. Said covering need not be substantially gas tight, particularly if the inert gas is supplied to the heaped pile under positive pressure. The inert gas may be applied to the closed space through one or more input ports in the covering.

In other embodiments, the delivery system for contacting the nutrient composition with the carbonaceous material in a reactor (or a bioreactor) comprises a conduit in fluid communication with the reactor (or bioreactor) for conveying the nutrient composition to the reactor, and a mixer. The mixer may be any suitable mixer capable of mixing a heterogeneous two phase mixture.

Collector for Collecting Methane

It will be appreciated by persons skilled in the art that the collector for collecting the methane will depend on whether the carbonaceous material may be an in situ carbonaceous material or an ex situ carbonaceous material.

In respect of in situ carbonaceous material, the collectors for collecting methane are well understood by those skilled in the art of recovering CSM and associated gas from various oil and gas bearing subterranean formations. For example, recovery wells may be drilled to recover methane from the in situ carbonaceous material. The recovery well may be in fluid communication with a compressor to compress the recovered methane, and a storage reservoir or transport conduit for natural gas distribution.

Similarly, in respect of ex situ carbonaceous material, various collectors for collecting methane are well understood by those skilled in the art of recovering biogas from reactors, bioreactors, heaped piles, and so forth. For example, the collector may comprise a shell disposed over the ex situ carbonaceous material, or any suitable covering such as a tarpaulin, to confine the biogenic methane in a headspace thereof. The covering may be provided with one or more ports therein in fluid communication with a pump and reservoir configured to withdraw methane from the headspace under positive or negative pressure.

It will be appreciated that the geometry of injection sites, laterals and recovery wells can be variable, but must be based on local geologic, structural, and hydrologic conditions in order to maximise the injection volumes of nutrient composition (concentrate) and to attain maximum recovery of methane. Additionally, at some point in time, the carbonaceous material between the injection sites or laterals and the recovery wells may become methanogenically unproductive. Subsequently, the recovery wells may be converted into injection sites and a new series of recovery wells may be drilled.

EXAMPLES

Non-limiting Examples of a nutrient composition and process for enhancing biogenic methane production will now be described.

Samples

The microbial consortium was obtained from a coal-seam formation water sample originating in the Surat Basin, Queensland, Australia. Two samples were obtained from that location, one large volume was collected in a plastic carboy, shipped to the lab, filter sterilised and used as medium. The second smaller sample was collected on site and immediately degassed by bubbling helium through it, followed by the addition of $Na_2S$ to retain the reducing conditions. After shipping to the lab, this was stored anoxically and used as the microbiological inoculum for experiments. The coal used as feedstock was a mixed Surat Basin coal of sub-bituminous maturity, and from around 500 to 700 meters subsurface, supplied by Origin Australia.

Microcosm Cultures

To examine the effects of nitrogen and phosphorus, in an anoxic chamber, 120 ml vials that included 20 ml sterile Surat formation water with 2 ml (~2 g) of Surat crushed coal (<1.2 mm>0.5 mm) were amended with the nitrogen and phosphorus concentrations described in Table 1. Media were reduced with the addition of 8 ml/l of 100 mM $Na_2S$. The headspace gas mixture in these vials was initially ~100% helium. Ammonium and phosphate were added to triplicate vials in the form of ammonium ($NH_4Cl$) and phosphate ($K_2HPO_4.3H_2O$) in varying concentrations (Table 1), finally 200 μl of the Surat formation water was added as inoculant. After nutrient composition addition, the flasks were sealed with butyl-rubber septa and aluminium crimps (Grace Davison Discovery Sciences, Illinois, USA) and removed from the anoxic glove box. Cultures were inverted and incubated in the dark at 42° C. Culture vials were incubated in an inverted position to minimise loss of gases through the butyl rubber septa. Three gas chromatography (GC) measurements of methane were undertaken at approximately 2, 4 and 6 weeks. After sampling, vials re-gassed with ~100% helium after sampling. Various controls were established, also in triplicate, using the same formation water.

TABLE 1

Nitrogen and phosphorus amendments (N:P, g/l) to the Surat basin coal/formation water mixtures.

| N (μM) | P (μM) | | | | | |
|---|---|---|---|---|---|---|
| | 0 | 219 | 438 | 876 | 1752 | 3504 |
| 0 | 0:0 | 0:50 | 0:100 | 0:200 | 0:400 | 0:800 |
| 238 | 12.5:0 | 12.5:50 | 12.5:100 | 12.5:200 | 12.5:400 | 12.5:800 |
| 476 | 25:0 | 25:50 | 25:100 | 25:200 | 25:400 | 25:800 |
| 953 | 50:0 | 50:50 | 50:100 | 50:200 | 50:400 | 50:800 |
| 1907 | 100:0 | 100:50 | 100:100 | 100:200 | 100:400 | 100:800 |
| 3814 | 200:0 | 200:50 | 200:100 | 200:200 | 200:400 | 200:800 |

Gas Measurement

Five ml gas samples were collected from septum sealed bottles via a gas-tight syringe. The composition of the culture gases were analysed on the Micro-GC. Samples were injected into the front injection port of the GC by syringe pump. The Micro-GC is equipped with three different column modules: 10 m Molsieve 5 Å column with backflush, a 10 m Pora Plot Q column with backflush and a 10 m CP-SiI-5CB column. Gases were detected using a micro machined thermal conductivity detector for each module; limit of detection is in the order of ~1 ppm. The injector has a built-in 10 μl sample loop and the helium carrier pressure was set to 15 psi and the injector temperature was 90° C. The temperature of the Molsieve 5A column in channel 1, the Pora Plot Q column in channel 2 and the CP-SiI-5CB column in channel 3 was set to 90° C., 70° C. and 60° C., respectively. After being injected into Micro-GC, gases are drawn by a vacuum pump through the sample loop and then the inlet system injects the gas sample from the sample loop into the carrier gas stream. $O_2/Ar$, $N_2$, $CH_4$ and CO are separated on the Molsieve 5A column. $CO_2$, $O_2H_6$ and $O_3H_8$ are separated on the Pora Plot Q column. C4-C5 hydrocarbon gases and $H_2S$ are separated on the CP-SiI-5CB column.

Results and Discussion.

Optimising the Nitrogen (N) and Phosphorus (P) Inputs.

Figure 1A:
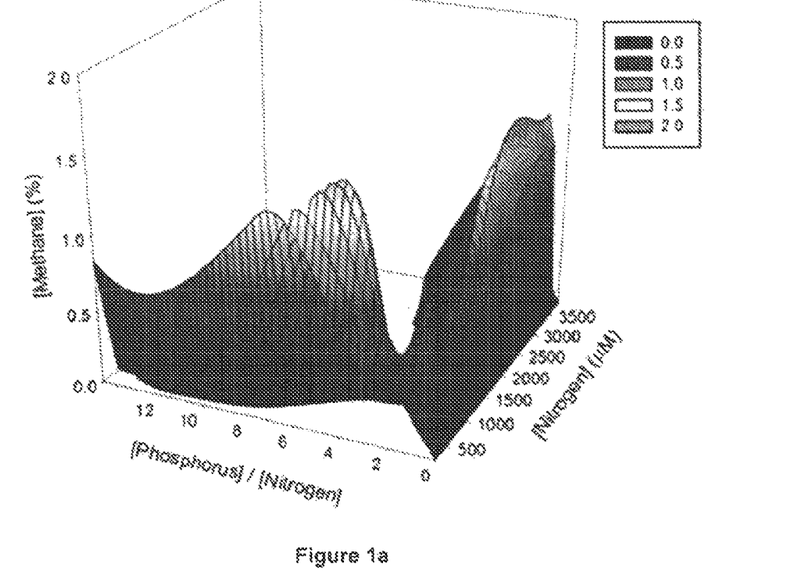
FIG. 1 is a 3D-interpolated mesh plot showing the effect of phosphorus to nitrogen ratio and nitrogen concentration in the nutrient composition on methanogenesis (as % methane in the headspace) of Surat coal by the Surat formation water consortium after four and six weeks incubation. The scatterplot data are smoothed in SigmaPlot v. 11.0 using a LOESS regression algorithm and an irregular mesh fitted to the shape; and, FIG. 2 is a 2D graph derived from data from the 3D graphs in FIG. 1 in which the source of phosphorous in the composition has a constant concentration of 1.90 mM $K_2HPO_4.2H_2O$ and the concentration of the source of nitrogen (e.g. $NH_4Cl$) varies.
Figure 1B:
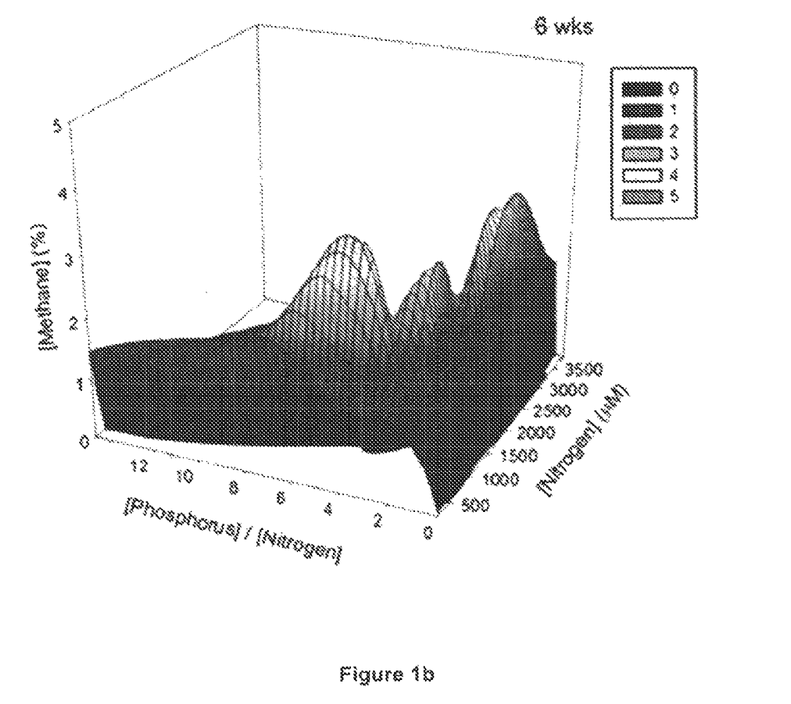

In this experiment, crushed sub-bituminous coal from the Surat basin was incubated with formation water which had been amended with various concentrations of $NH_4Cl$ and or $K_2HPO_4$ under an argon atmosphere. Headspace gas was analysed every two weeks for six weeks. In general gas production increased with time. The results methane at weeks 4 and 6 are given in Table 2. Treatments were established in triplicate. In the absence of additional N and P, $CH_4$ production was minimal. As the concentration of N increases, unless P is present no increase in methanogenesis was observed. In contrast, when P is present in the absence of N, there is a small amount of methanogenesis, which presumably indicates there is sufficient N available in the formation water or the coal to allow some cell growth and methanogenesis. Indeed, addition of N may not provide any benefit beyond the lowest level of supplementation, 238 μM $NH_4Cl$, used in this experiment. In contrast, provided some N is added, addition of P has a dramatic effect on the yield of $CH_4$ (FIG. 1). The highest yields of $CH_4$ are obtained at the highest concentrations of P (~1-3.5 mM). In these greater concentrations of P, it seems likely that a small amount of N is all that is required to facilitate early growth of cells, after this initial N is depleted, the microbes may be able to obtain sufficient N from the coal itself to facilitate their continued growth. The coals used in this study were typically composed of between 1 and 2.4 wt % N on a dry ash-free basis.

As nitrogen levels increase the additional nitrogen availability is thought to stimulate the growth of non-productive (in terms of $CH_4$ production) microflora which compete with the methanogenic pathway for energy and carbon or hydrogen.

It is surprising that relatively little N compared to P is required to produce optimal yields of methane. It is well established that the macro-chemical composition of "typical" bacteria and archaea are in the molar ratio range (C:N:P) 102:12:1 or in the case of P depleted conditions 259:69:1 (Cotner et al 2010). That is, the amount of N in a microorganism exceeds the amount of P by more than a factor of 10 even under P replete conditions. Hence, we expected that more N than P may have been required for optimal growth of microbes and production of methane.

Mean yields of methane (% headspace gas) for all concentrations and P/N ratios derived from experiments performed in triplicate are shown in Table 2. Triplicate data is plotted in FIG. 1 as an interpolated meshplot showing the effect of phosphorus to nitrogen molar ratio and nitrogen molar concentration on methanogenesis. The data in FIG. 1 has been smoothed in SigmaPlot v.11.0 using a LOESS regression algorithm (Cleveland, 1979) and an irregular mesh has been fitted to the shape. The algorithm has removed statistically generated anomalies arising from experimental variation and incidences of experiment failure. This approach attempts to describe a general observed trend whilst avoiding excessive distortion caused by outliers.

Data has been corrected for desorption, by subtracting the observed concentration of each gas in a treatment in which the microbial population has been killed by the addition of 70 v/v % ethanol.

TABLE 2

| μM [N] | μM [P] | [P]/[N] | [CH$_4$] 4 weeks | [CH$_4$] 6 weeks |
|---|---|---|---|---|
| 0 | 876 | — | 0.28 | 0.31 |
| 238 | 876 | 3.68 | 0.58 | 1.29 |
| 476 | 876 | 1.84 | 0.53 | 1.44 |
| 953 | 876 | 0.92 | 0.43 | 0.90 |
| 1907 | 876 | 0.46 | 0.41 | 0.57 |
| 3814 | 876 | 0.23 | 0.34 | 0.52 |
| 0 | 1752 | — | 0.08 | 0.09 |
| 238 | 1752 | 7.36 | 1.32 | 2.26 |
| 476 | 1752 | 3.68 | 1.35 | 3.51 |
| 953 | 1752 | 1.84 | 0.49 | 2.81 |
| 1907 | 1752 | 0.92 | 1.05 | 2.67 |
| 3814 | 1752 | 0.46 | 0.66 | 0.75 |
| 0 | 3504 | — | 0.25 | 0.23 |
| 238 | 3504 | 14.72 | 0.84 | 1.45 |
| 476 | 3504 | 7.36 | 0.83 | 2.29 |
| 953 | 3504 | 3.67 | 0.21 | 1.09 |
| 1907 | 3504 | 1.84 | 0.25 | 1.51 |
| 3814 | 3504 | 0.92 | 1.34 | 1.46 |

Figure 2:
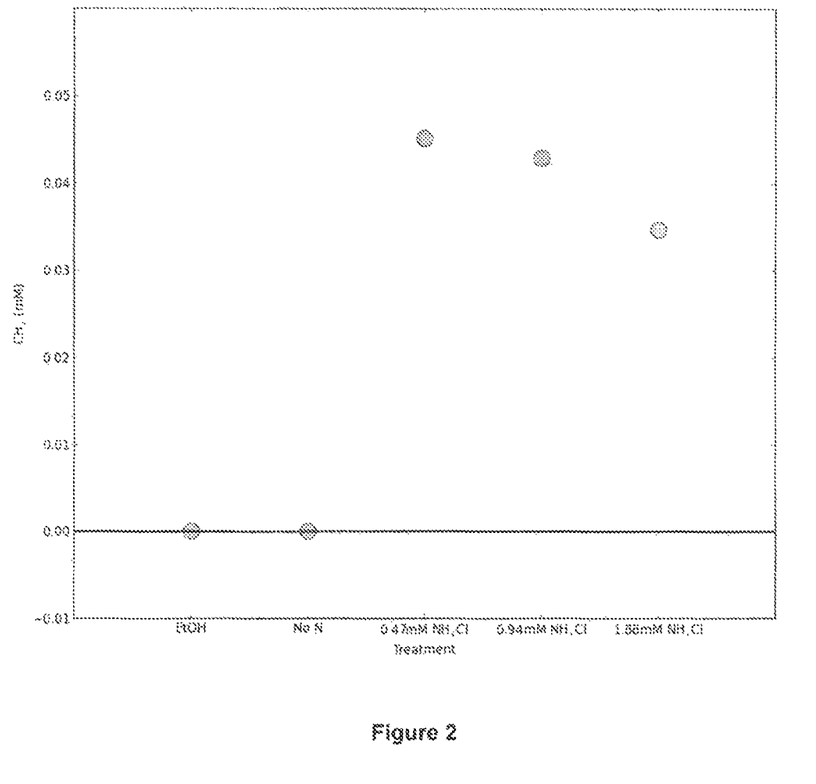

FIG. 2 is a 2D graph derived from data from the 3D graphs in FIG. 1 in which the source of phosphorous in the composition has a constant concentration of 1.90 mM K$_2$HPO$_4$.2H$_2$O and the concentration of the source of nitrogen (e.g. NH$_4$Cl) varies. The results indicate that the production of methane declines if the concentration of nitrogen in the nutrient composition exceeds 1.7 mM.

In some samples, methane production declined or ceased after at least three weeks had expired since the sample was dosed with the nutrient composition. In samples where there was declining methane production, a dose of a second nutrient composition containing phosphorus (i.e. in the absence of N or with negligible N) was introduced to the samples, thereby restoring methane production to comparable levels to those observed after the initial dose of the nutrient composition. Subsequent doses of the second nutrient composition were introduced at intervals when methane production began to decline. Restoration of methane production to comparable levels were observed.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Further, with regard to the various means referred to throughout the specification, any means is to be understood as encompassing individual as well as plural structures that may or may not be physically connected.

REFERENCES

Li D, Hendry P, Faiz M. (2008) A survey of the microbial populations in some Australian coalbed methane reservoirs. *International Journal of Coal Geology*, 76, 14-24.

The invention claimed is:

1. A process for enhancing biogenic methane production from a carbonaceous material, the process comprising the steps of:
    contacting a first nutrient composition with the carbonaceous material for a period of time to biogenically produce methane, the first nutrient composition comprising a source of phosphorus (P) and a source of nitrogen (N), wherein the molar ratio of phosphorus to nitrogen (P/N) is greater than 2 and the nitrogen concentration is at least 0.1 mM and less than 1 mM; and,
    collecting methane from the carbonaceous material,
    wherein the carbonaceous material is a carbon-containing substance capable of supporting one or more methanogenic microbial populations, and wherein the carbonaceous material is subject to degradation by the one or more methanogenic microbial populations to produce methane or methane precursors.

2. The process according to claim 1, further comprising the step of contacting a second nutrient composition with the carbonaceous material for a period of time to biogenically produce methane, said second nutrient composition contacting the carbonaceous material after said first nutrient composition contacts the carbonaceous material.

3. The process according to claim 2, wherein the second nutrient composition comprises a P/N molar ratio greater than the P/N molar ratio of the first nutrient composition or wherein the second nutrient composition comprises substantially no nitrogen.

4. The process according to claim 2, wherein the period of time between the contacting of the first and second nutrient compositions with the carbonaceous material is at least 1 week.

5. The process according to claim 2, wherein the carbonaceous material is an in situ carbonaceous material, and wherein contacting said first and/or second nutrient composition with the carbonaceous material comprises injecting the nutrient composition into or proximal to the in situ carbonaceous material or co-injecting the nutrient composition with a hydraulic fracturing fluid.

6. The process according to claim 1, wherein the first nutrient composition is delivered by injecting a concentrate to the carbonaceous material, whereby the concentrate undergoes dilution with fluids associated with the carbonaceous material to provide a first nutrient composition having an effective P/N molar ratio greater than 2 and an effective nitrogen concentration of at least 0.1 mM and less than 1 mM.

7. The process according to, claim 1, wherein, the carbonaceous material is an ex situ carbonaceous material in a heaped pile, and wherein contacting said nutrient composition with the carbonaceous material comprises applying the nutrient composition to an outer surface of the heaped pile in an amount sufficient to cause the nutrient composition to flow or trickle under gravity from the outer surface through underlying carbonaceous material in the heaped pile.

8. The process according to claim 1, wherein the carbonaceous material is an ex situ carbonaceous material in a reactor, and wherein contacting said nutrient composition with the carbonaceous material comprises mixing the nutrient composition with the carbonaceous material in the reactor.

9. The process according to claim 8, wherein the mixing is continuous, intermittent, or ceases entirely after an initial mixing period, said period being sufficient to bring the nutrient composition into contact with the carbonaceous material.

10. The process according to claim 1, wherein the first nutrient composition further comprises one or more methanogenic microbial populations.

11. The process according to claim 1, wherein the molar ratio of phosphorus to nitrogen (P/N) is less than 8.

12. The process according to claim 1, wherein the nitrogen concentration is at least 0.2 mM.

13. The process according to claim 1, wherein the first nutrient composition comprises a phosphorus concentration of at least 1 mM.

14. The process according to claim 1, wherein the first nutrient composition further comprises at least one trace element selected from the group consisting of iron, manganese, cobalt, zinc, molybdenum, nickel, aluminium, boron, copper, tungsten and selenium, and/or at least one vitamin selected from the group consisting of pyridoxine, aminobenzoic acid, pantothenate, nicotinic acid, riboflavin, thiamine, thioctic acid, biotin, folic acid, pyruvate and B12, and/or at least one additive selected from the group consisting of acids, bases, buffering agents, oxidants, anti-oxidants, surfactants, emulsifying agents, gelling agents, and any combination thereof.

15. The process according to claim 1, wherein the carbonaceous material is selected from the group consisting of coal, lignite, peat, drill cuttings, waste coal, coal derivatives, oil shale, oil formations, tar sands, hydrocarbon-contaminated soil and petroleum sludges.

16. A process for enhancing biogenic methane production from a carbonaceous material, the process comprising the steps of:
contacting a nutrient composition with the carbonaceous material for a period of time to biogenically produce methane, the nutrient composition comprising a source of phosphorus (P) and a source of nitrogen (N), wherein the molar ratio of phosphorus to nitrogen (P/N) is greater than 1.5 and the nitrogen concentration is at least 0.1 mM and less than 1.7 mM, and,
collecting methane from the carbonaceous material,
wherein the carbonaceous material is a coal deposit, coal, lignite, peat, drill cutting, waste coal, a coal derivative, oil shale, oil formation, tar sand, hydrocarbon-contaminated soil and petroleum sludge, or a combination thereof.

17. The process of claim 16, wherein the nutrient composition further comprises one or more methanogenic microbial populations.

18. The process of claim 16, wherein the molar ratio of phosphorus to nitrogen (P/N) is less than 8.

19. The process of claim 16, wherein nitrogen concentration is at least 0.2 mM.

20. The process of claim 16, wherein the nitrogen concentration is less than 1.5 mM.

21. The process of claim 16, wherein the nutrient composition comprises a phosphorus concentration of at least 1 mM.

22. The process of claim 16, wherein the nutrient composition further comprises at least one trace element selected from the group consisting of iron, manganese, cobalt, zinc, molybdenum, nickel, aluminium, boron, copper, tungsten and selenium, and/or at least one vitamin selected from the group consisting of pyridoxine, aminobenzoic acid, pantothenate, nicotinic acid, riboflavin, thiamine, thioctic acid, biotin, folic acid, pyruvate and B12, and/or at least one additive selected from the group consisting of acids, bases, buffering agents, oxidants, anti-oxidants, surfactants, emulsifying agents, gelling agents, and any combination thereof.

* * * * *